United States Patent [19]

Weaver et al.

[11] Patent Number: 4,749,772

[45] Date of Patent: Jun. 7, 1988

[54] CONDENSATION COPOLYMERS CONTAINING METHINE ULTRAVIOLET RADIATION-ABSORBING RESIDUES AND SHAPED ARTICLES PRODUCED THEREFROM

[75] Inventors: Max A. Weaver; Wayne P. Pruett, both of Kingsport; Samuel D. Hilbert, Jonesborough, all of Tenn.

[73] Assignee: Eastman Kodak Company, Rochester, N.Y.

[21] Appl. No.: 75,389

[22] Filed: Jul. 20, 1987

[51] Int. Cl.[4] .................. C08G 63/44; C08G 69/44; C08G 63/76
[52] U.S. Cl. ........................ 528/288; 525/445; 525/46; 528/290; 528/302; 528/303; 528/304; 528/183; 528/192; 528/193; 528/194
[58] Field of Search ............ 528/288, 290, 302, 303, 528/304, 183, 192–194; 525/46, 445

[56] References Cited

U.S. PATENT DOCUMENTS

| | | | |
|---|---|---|---|
| 3,597,434 | 8/1971 | Weaver | 546/165 |
| 4,297,502 | 10/1981 | Herrmann et al. | 528/288 X |
| 4,338,247 | 7/1982 | Zannucci et al. | 528/307 |
| 4,617,373 | 10/1986 | Pruett et al. | 528/288 |

*Primary Examiner*—Lucille M. Phynes
*Attorney, Agent, or Firm*—J. Frederick Thomsen; William P. Heath, Jr.

[57] ABSTRACT

A composition useful for molding into articles such as food containers, soft drink bottles, cured structural plastics and the like, comprising molding or fiber grade linear or unsaturated polyester or polycarbonate having copolymerized therein a total of from 1.0 to about 5,000 ppm, of the residue of one or a mixture of methine reactants of the formula

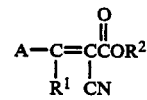

wherein A is an unsubstituted or substituted 2-furanyl, 2-thienyl or 3-thienyl radical;
$R^1$ is hydrogen or a unsubstituted or substituted alkyl, cycloalkyl or aryl radical; and
$R^2$ is hydrogen or an unsubstituted or substituted alkyl, alkenyl, cycloalkyl or aryl radical.

The methine residues are present in the polymer as an integral part of the polymer chain and absorb ultraviolet radiation in the range of about 150 to about 390 nm. The residues are non-extractable from the polymer and stable at the conditions at which the polymers are manufactured and processed.

19 Claims, No Drawings

CONDENSATION COPOLYMERS CONTAINING METHINE ULTRAVIOLET RADIATION-ABSORBING RESIDUES AND SHAPED ARTICLES PRODUCED THEREFROM

DESCRIPTION

TECHNICAL FIELD

This invention concerns condensation polymers, including linear, thermoplastic polyesters, unsaturated polyesters and polycarbonates, wherein the polymer contains, as an integral part of the polymer backbone or chain, certain ultraviolet (UV) light absorbing residues derived from certain methine compounds which are reacted with the polymer or polymer precursors, i.e., prepolymer or monomers. The methine residues and the compounds from which they are derived are thermally stable and nonsublimable at the polymer preparation and processing temperatures. The methine residues are nonextractable from the polymers, do not discolor the polymers, and absorb UV radiation. The polymers and shaped articles are particularly useful in packaging beverages, pharmaceuticals and cosmetics subject to degradation from UV radiation. The methine residues are useful in total concentrations ranging from about 1.0 to about 10,000 parts per million (ppm), preferably 2.0 to about 1,500 ppm, and most preferably from about 200 to about 800 ppm (parts by weight of methine residue per million parts by weight of final polymer).

Many products such as certain fruit juices, soft drinks, wines, food products, cosmetics and shampoos are deleteriously affected by UV light when packaged in clear (essentially colorless and transparent) plastic containers which pass significant portions of light having wavelengths of about 250 to about 390 nm. Heretofore, various UV absorbers such as the benzophenones, benzotriazoles and resorcinol monobenzoates have been incorporated into polymers as discussed in Plastics Additives Handbook, Hanser Publishers, Library of Congress Catalog No. 83-062289, pp 128–134, for use in absorbing or screening deleterious radiation. Although the additives function well to screen radiation in the range of from about 300 to about 330 nm, this range is not adequate to protect the contents of food packaging produced from these polymers. Moreover, such compounds, when physically blended with polyesters are extractable by materials which may be present in food packaged with the polymers. Such solvents would include typical food acids, alcohols and the like. Furthermore, these compounds are not stable under the polyester manufacturing and processing conditions and produce objectionable yellow shades in food packaging.

U.S. Pat. Nos. 3,634,320, 4,305,719, 4,338,247, 4,340,718 and 4,617,374 disclosed the concept of reacting benzylidene-type methine compounds capable of absorbing UV light with or into polyesters. These patents do not, however, disclosed the use of the methine compounds described hereinafter to obtain the compositions provided by this invention.

DISCLOSURE OF INVENTION

We have found that polyesters and polycarbonates containing the residue of one or more of the methine compounds described hereinbelow can be used in the manufacture of containers and other shaped articles and that such containers and articles absorb harmful radiation of the wavelength referred to above. Thus, UV light degradation of materials packaged in the containers and articles is reduced or eliminated. When used in low concentrations, e.g., 200 to 800 ppm, the methine residues derived from the methine compounds described below impart to the polymers the property of UV or visible light absorption within the range of from about 250 nm to about 390 nm. The methine residue reacts with the polymer chain or backbone, for example, through an ester group of the methine compounds from which the residue is derived. The methine compounds and residues are thermally stable at polymer processing conditions, which includes polycondensation temperatures of up to about 300° C. which are used, for example, in the preparation of polyesters such as poly(ethylene terephthalate) and copolymers of terephthalic acid, ethylene glycol, and 1,4-cyclohexanedimethanol.

The concentration of the methine moieties may be increased to higher levels such as 5,000 ppm or higher, to provide polymers which exhibit improved resistance to weathering. Furthermore, when these polymers per se or fibers thereof are dyed with disperse dyes at a concentration, for example, of from about 0.01 to about 5.0% based on weight of polymer or fiber, the dyed polymer of fibers may exhibit increased lightfastness. Such disperse dyes are shown, for example, in U.S. Pat. Nos.: 4,305,719; 2,746,952; 2,746,953, 2,757,173; 2,763,668; 2,771,466; 2,773,054; 2,777,863; 2,785,157; 2,790,791; 2,798,081; 2,805,218; 2,822,359; 2,827,450; 2,832,761; 2,852,504; 2,857,371; 2,865,909; 2,871,231; 3,072,683; 3,079,373; 3,079,375; 3,087,773; 3,096,318; 3,096,322; 3,236,843; 3,254,073; 3,349,075; 3,380,990; 3,386,990; 3,394,144; 3,804,823; 3,816,388; 3,816,392; 3829,410; 3,917,604; 3,928,311; 3,980,626; 3,998,801; 4,039,522; 4,052,379; and 4,140,683, the disclosures of which are incorporated herein by reference.

The present invention is defined in its broad embodiment as a composition comprising molding or fiber grade condensation polymer having copolymerized therein a total of from 1.0 to about 10,000 ppm, of a residue of one or more of methine compounds of the formula

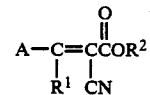

ps wherein A is an unsubstituted or substituted 2-furanyl, 2-thienyl or 3-thienyl radical;

R¹ is hydrogen or an unsubstituted or substituted alkyl, cycloalkyl or aryl radical;

R² is hydrogen or an unsubstituted or substituted alkyl, alkenyl, cycloalkyl or aryl radical.

When one or more of the methine compounds are allowed to react with the monomers used in the preparation of the polyesters or a prepolymer derived from the monomers, a methine residue of the compounds forms an integral part of the final polyester, e.g.

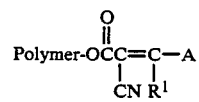

The furanyl and thienyl radicals represented by A typically have the formula

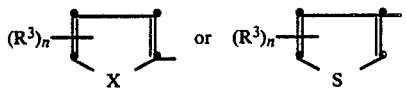

wherein $R^3$ is alkyl; substituted alkyl such as hydroxyalkyl, alkoxyalkyl, alkanoyloxyalkyl, arylalkyl, aryloxyalkyl, etc.; alkenyl; alkoxy; cycloalkyl; aryl; alkylthio; arylthio; or halogen;

X is oxygen or sulfur; and n is 0, 1 or 2.

Examples of the substituted alkyl groups which $R^1$ and $R^2$ can represent include haloalkyl, alkanoylamidoalkyl, cyclohexylalkyl, cyanoalkyl, hydroxyalkoxyalkyl, furfuryl, as well as those set forth in the above definition of $R^3$. The unsubstituted and substituted alkyl groups and the alkyl moieties of the other alkyl-containing groups which $R^1$, $R^2$ and $R^3$ can represent generally may contain up to about 12 carbon atoms, preferably up to about 6 carbon atoms. The aryl groups set forth in the definitions of $R^1$, $R^2$ and $R^3$ typically may be phenyl or phenyl substituted with alkyl, alkoxy, halogen, etc. The alkenyl groups may contain from 2 to about 8 carbon atoms while the cycloalkyl radicals can contain from 5 to 7 carbon atoms.

The methine compounds can be prepared using known procedures by reacting an intermediate carbonyl compound II with an active methylene compound III under Knovenagel reaction conditions, e.g.

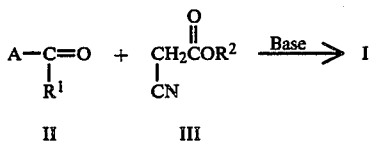

Usually the reaction may be conducted in the presence of an inert solvent such as methanol, ethanol or 2-propanol. When $R^1$ is not hydrogen, it may be advantageous to use a hydrocarbon solvent such as benzene or toluene to allow the water of reaction to be removed azeotropically as it is formed. Examples of the bases which may be used to promote the reaction include piperidine, piperidine acetate, sodium acetate and pyridine.

The compounds of Formula I which are particularly preferred in preparing the novel compositions provided by this invention have the formula

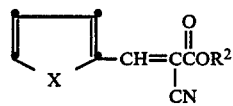

wherein X is oxygen or sulfur and $R^2$ is lower alkyl, i.e. alkyl containing up to about 4 carbon atoms, especially methyl or ethyl.

The polyesters which may be used in the preparation of the compositions of our invention include linear, thermoplastic, crystalline or amorphous polyesters produced by conventional polymerization techniques from one or more diols and one or more dicarboxylic acids. The polyesters normally are molding or fiber grade and have an inherent viscosity (IV) of about 0.4 to about 1.2. The preferred polyesters comprise at least about 50 mole percent terephthalic acid residues and at least about 50 mole percent ethylene glycol and/or 1,4-cyclohexanedimethanol residues. Particularly preferred polyesters are those containing from about 75 to 100 mole percent terephthalic acid residues and from about 75 to 100 mole percent ethylene glycol residues.

The unsaturated, curable polyesters which may be used in our novel compositions are the polyesterification products of one or more glycols and one or more unsaturated dicarboxylic acids or their anhydrides. Typical of the unsaturated polyesters is the polyesterification product of (a) 1,4-cyclohexanedimethanol and-/or 2,2-dimethyl-1,3-propanediol and optionally an additional dihydric alcohol, such as ethylene glycol, and (b) maleic acid or fumaric acid and an aromatic dicarboxylic acid, which when crosslinked with an ethylenically-unsaturated monomer, e.g., styrene, produces a cured polyester resin which has, for example, high thermal resistance, high heat distortion values, excellent electrical and methanical properties, and excellent resistance to chemicals.

Solutions of such unsaturated polyester resins in an ethylenically-unsaturated monomer such as styrene commonly are referred to as polyester resins.

The unsaturated polyester resins may be prepared in the presence of gelation inhibitors such as hydroquinone or the like, which are well known in the art of polyesterification. The esterification may be carried out for example under an inert blanket of gas such as nitrogen in a temperature range of 118°-220° C. for a period of about 6-20 hours until an acid number below 100 and preferably below 50 is obtained, based on milliequivalents of KOH necessary to neutralize 1 gram of the unsaturated polyester. The resulting polyester may be subsequently copolymerized, crosslinked, or cured with "curing amounts" of any of the well-known ethylenically unsaturated monomers used as solvents for the polyester. Examples of such monomers include styrene, alpha-methyl styrene, vinyl toluene, divinyl benzene, chlorostyrene, and the like as well as mixtures thereof. Typically, the mole ratio of such unsaturated monomer to the unsaturated moiety (e.g., maleic acid residue) in the polyester is from about 0.5 to about 3.0, although the "curing amounts" of such monomer can be varied from these ratios.

It is preferred that the unsaturated polyester be prepared from one or more dihydric alcohols, fumaric or maleic acid or mixtures thereof, and up to about 60 mole percent of total acid component of o-phthalic, isophthalic or terephthalic acids or mixtures thereof. Preferred for the dihydric alcohol component is one or a mixture of propylene glycol, neopentyl glycol, 2,2,4-trimethyl-1,3-pentanediol, ethylene glycol, or diethylene glycol. A specific preferred unsaturated polyester is prepared from about 75 to 100 mole percent propylene glycol, and as the acid component, from about 75 to 100 mole percent o-phthalic and maleic acids in a mole ratio of from about ½ to about 2/1. Typical of these unsaturated polyesters are those disclosed, for example, in U.S. Pat. No. 4,359,570 incorporated herein by reference.

The diol components of the described polyesters may be selected from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, 1,3-cyclohexanedimethanol, X,8-bis(hydroxymethyl)-tricyclo-[5.2.1.0]-decane wherein X represents 3, 4, or 5; and diols containing one or more oxygen atoms in the chain, e.g., diethylene glycol, triethylene glycol, dipropylene glycol, tripropylene glycol and the like. In general, these diols contain 2 to 18, preferably 2 to carbon atoms. Cycloaliphatic diols can be employed in their cis or trans configuration or as mixtures of both forms.

The acid components (aliphatic, alicyclic, or aromatic dicarboxylic acids) of the linear polyester are selected, for example, from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalene-dicarboxylic acid and the like. In the polymer preparation, it is often preferable to use a functional acid derivative thereof such as the dimethyl, diethyl, or dipropyl ester of the dicarboxylic acid. The anhydrides or acid halides of these acids also may be employed where practical.

Typical polycarbonates useful herein are disclosed in Kirk-Othmer Encyclopedia of Chemical Technology, third edition, Volume 18, pages 479-494, incorporated herein by reference.

The noval polymer compositions provided by this invention are useful in the manufacture of containers or packages for comestibles such as beverages and food. By the use of known heat-setting techniques, certain of the polyesters are, in terms of color, I.V. and heat distortion, stable at temperatures up to about 100° C. Such stability characteristics are referred to herein as "hot-fill" stability. Articles molded from these polyesters exhibit good thin-wall rigidity, excellent clarity and good barrier properties with respect to moisture and atmospheric gases, particularly carbon dioxide and oxygen.

The linear polyesters most preferred for use in articles having "hot-fill" stability comprise poly(ethylene terephthalate) and poly(ethylene terephthalate) wherein up to 5 mole percent of the ethylene glycol residues have been replaced with residues derived from 1,4-cyclohexanedimethanol, wherein the polyesters have been sufficiently heat set and oriented by methods well known in the art to give a desired degree of crystallinity. By definition, a polymer is "hot-fill" stable at a prescribed temperature when less than 2% change in volume of a container manufactured therefrom occurs upon filling the same with a liquid at that temperature. For the manufacture of blow-molded beverage bottles, the most preferred polyesters have an I.V. of 0.65 to 0.85, and a Tg of >70° C., and film sections cut from the bottle have a Water Vapor Transmission Rate of 1.5 to 2.5 g. mils/100 in.$^2$-24 hrs. a Carbon Dioxide Permeability of 20-30 cc. mils/100 in.$^2$-24 hrs.-atm., and an Oxygen Permeability of 4-8 cc. mils/100 in.$^2$-24 hrs.-atm. The Tg is determined by Differential Scanning Calorimetry at a scan rate of 20 Centigrade Degrees/min., the Oxygen Permeability by the standard operating procedure of a MOCON OXTRAN 100 instrument of Modern Controls, inc., of Elk River, Minn., and the Carbon Dioxide Permeability by the standard operating procedure of a MOCON PERMATRAN C II, also of Modern Controls.

The preparation of the methine compound and their use in preparing the compositions of our invention are further illustrated by the following examples.

EXAMPLE 1

Ethyl cyanoacetate (4.52 g; 0.04 mol), 2-furaldehyde (3.84 g; 0.04 mol) ethyl alcohol (30 mL), and piperidine (10 drops) are mixed and heated at reflux for 3 hours. Upon cooling, a pale yellow crystalline product precipitates which is collected by filtration, washed with ethanol, and finally recrystallized from ethanol. The yield is 4.5 g of product, which mass spectrometry analysis confirmed is ethyl 2-cyano-3-(2-furanyl)-2-propenoate. In the ultra-violet absorption spectrum, the compound had an absorption maximum at 336 nm in methylene chloride.

EXAMPLE 2

2-Thiophenecarboxaldehyde (5.61 g, 0.05 mol), ethyl cyanoacetate (5.66 g, 0.05 mol), ethanol (50 mL) and piperidine (10 drops) are mixed and heated at reflux for 2.5 hr. The pale yellow product is isolated by cooling the reaction solution and filtering and is washed with ethanol and dried in air (yield-8.5 g). In methylene chloride the compound has an absorption maximum ($\lambda$ max ) at 341 nm in the ultra-violet absorption spectrum. The structure of the product, ethyl 2-cyano-3-(2-thienyl)-2-propenoate, is confirmed by mass spectrometry.

EXAMPLE 3

A mixture of 5-chloro-2-thiophenecarboxyaldehyde (2.94 g, 0.02 mol), ethyl cyanoacetate (2.26 g, 0.02 mol), ethanol (40 mL), and piperidine (5 drops) is heated at reflux for about 1 hr. Upon cooling, the pale yellow product crystallizes and is collected by filtration, washed with ethanol, and dried in air (yield-3.0 g). The product, ethyl 2-cyano-3-(5-chloro-2-thienyl)-2-propenoate, has an absorption maximum ($\lambda$ max) at 345 nm in the ultra-violet absorption spectrum when dissolved in acetone.

EXAMPLE 4

3-Thiophenecarboxaldehyde (5.61 g, 0.05 mol) is reacted with ethyl cyanoacetate (5.66 g, 0.05 mol) according to the reaction conditions described in Example 2 and the white product (yield 3.0 g) isolated in a similar manner. It has an absorption maximum ($\lambda$ max at 313 nm) in the ultra-violet absorption spectrum in methylene chloride. Mass spectrometry analysis confirms that the product is ethyl 2-cyano-3-(3-thienyl)-2-propenoate.

EXAMPLE 5

The following materials are placed in a 500-mL, three-necked, round-bottom flask:
  97 g (0.5 mol) dimethyl terephthalate
  62 g (1.0 mol) ethylene glycol
  0.00192 g Ti from a n-butanol solution of acetyl-triisopropyl titanate
  0.0053 g Mn from an ethylene glycol solution of manganese acetate
  0.0345 g antimony trioxide
  0.0072 g Co from an ethylene glycol solution of cobaltous acetate The flask is equipped with a nitrogen inlet, stirrer, vacuum outlet, and condensing flask. The flask and contents are heated at 200° C. in a Belmont metal bath for 60 minutes and at 210° C. for 75 minutes with a nitrogen sweep over the reaction mixture. Then 1.57 mL of an ethylene glycol slurry of a mixed phosphorus ester composition (Zonyl A) which contains 0.012 g phosphorus is added. The temperature of the bath is increased to 230° C. At 230° C., ethyl 2-cyano-3-(2-furanyl)-2-propenoate (0.0384 g) is added to the flask. Five minutes after this addition, a vacuum with a slow stream of nitrogen bleeding in the system is applied over a five-minute period until the pressure is reduced to 200 mm Hg. The flask and contents are heated at 230° C. under a pressure of 200 mm Hg for 25 minutes. The metal bath temperature is increased to 270° C. At 270° C. the pressure is reduced slowly to 100 mm Hg. The flask and contents are heated at 270° C. under a pressure of 100 mm Hg for 30 minutes. The metal bath temperature is increased to 285° C. and the pressure is reduced slowly to 4.5 mm Hg. The flask and contents are heated at 285° C. under pressure of 4.5 mm Hg for 25 minutes.

Then the pressure is reduced to 0.25 mm Hg and polycondensation is continued for 40 minutes. The flask is removed from the metal bath and is allowed to cool in a nitrogen atmosphere while the polymer crystallizes. The resulting polymer has an inherent viscosity of 0.52 measured in a 60/40 ratio by weight of phenol/tetrachloroethane at a concentration of 0.5 g per 100 mL. An amorphous 13 mil thick film molded from this polymer to simulate the sidewall of a container transmits less than 10% light from 250 to 365 nm where a 13 mil film prepared from a like polyester without the copolymerized absorber transmits greater than 10% light at all wavelengths above 320 nm.

The same results are obtained when the methine compound used in Example 5 is replaced with ethyl 2-cyano-3-(2-thienyl)-2-propenoate.

Additional examples of methine compounds which may be used to prepare our novel polymer compositions are set forth in the following Tables. These compounds can be prepared according to the procedures described hereinabove and conform to the formulas given.

TABLE I

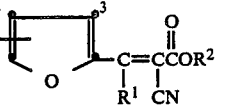

| Example | $(R^3)_n$ | $R^1$ | $R^2$ |
|---|---|---|---|
| 6 | H | —CH$_3$ | —CH$_3$ |
| 7 | H | —C$_6$H$_5$ | —C$_2$H$_5$ |
| 8 | H | —C$_6$H$_{11}$ | —CH(CH$_3$)$_3$ |
| 9 | 3-CH$_3$ | H | —CH$_3$ |
| 10 | 4-CH$_3$ | H | —CH(CH$_3$)$_2$ |
| 11 | 5-CH$_3$ | H | —CH$_2$CH$_2$OH |
| 12 | 4,5-di-CH$_3$ | H | —CH$_2$CH$_2$OC$_2$H$_5$ |
| 13 | 5-CH$_2$CH=CH$_2$ | H | —CH$_2$CH$_2$OCCH$_3$ (O) |
| 14 | 5-C$_6$H$_{11}$ | H | —CH$_2$CH$_2$Cl |
| 15 | 5-CH$_3$—4-CH$_2$C$_6$H$_5$ | H | —CH$_2$CH$_2$NHCCH$_3$ (O) |
| 16 | 5-CH$_2$C$_6$H$_5$ | H | —CH$_2$CH$_2$C$_6$H$_5$ |
| 17 | 5-OCH$_2$C$_6$H$_5$ | H | —CH$_2$C$_6$H$_{11}$ |
| 18 | 4-CH$_3$—5-(C$_6$H$_4$—4-CH$_3$) | H | —CH$_3$ |
| 19 | 5-CH$_2$OCH$_3$ | H | —CH$_2$CH$_2$CN |
| 20 | 5-CH$_2$OH | H | —C$_6$H$_{11}$ |
| 21 | 4,5-di-CH$_2$OH | H | —C$_6$H$_5$ |
| 22 | 5-OCH$_3$ | H | —CH$_2$OC$_6$H$_5$ |
| 23 | 4-OCH$_3$ | H | —CH$_2$CH$_2$OC$_6$H$_5$ |
| 24 | 5-OC$_6$H$_5$ | H | —CH$_2$CH$_2$OCH$_2$CH$_2$OH |
| 25 | 5-S(CH$_2$)$_3$CH$_3$ | H | —CH$_2$C$_6$H$_5$ |
| 26 | 5-CH$_2$OCCH$_3$ (O) | H | —CH$_3$ |
| 27 | 5-SC$_6$H$_5$ | H | —CH$_2$CH(OH)CH$_3$ |
| 28 | H | H | H |
| 29 | 5-SCH$_2$C$_6$H$_5$ | H | —CH$_2$C$_6$H$_{10}$—4-CH$_2$OH |
| 30 | 4,5-di-CH$_2$OCCH$_3$ (O) | H | —C$_6$H$_5$ |
| 31 | 5-Cl | H | —CH$_3$ |
| 32 | 3,4-di-Cl | H | —CH$_3$ |
| 33 | 5-OC(CH$_3$)$_3$ | H | —(CH$_2$)$_3$CH$_3$ |
| 34 | 5-(C$_6$H$_4$—4-Cl) | H | —CH$_3$ |
| 35 | 5-(C$_6$H$_4$—4-CH$_3$) | H | CH$_3$ |

TABLE II

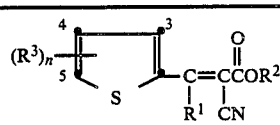

| Example | $(R^3)_n$ | $R^1$ | $R^2$ |
|---|---|---|---|
| 36 | H | —CH$_3$ | —CH$_3$ |
| 37 | H | —C$_6$H$_{11}$ | —CH$_3$ |

TABLE II-continued

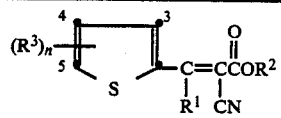

| Example | (R³)ₙ | R¹ | R² |
|---|---|---|---|
| 38 | H | —C₆H₅ | —CH₃ |
| 39 | 5-CH₃ | H | —CH₃ |
| 40 | 3,5-di-CH₃ | H | —CH₂CH₂CH₃ |
| 41 | 5-C(CH₃)₃ | H | —CH₂CH₂OH |
| 42 | 5-C₆H₅ | H | —CH(CH₃)₂ |
| 43 | 5-CH=CH₂ | H | —CH₂CH₂Cl |
| 44 | 4,5-di-CH₃ | H | —CH₂CH₂OC₂H₅ |
| 45 | 5-O(CH₂)₃CH₃ | H | —CH₃ |
| 46 | 5-OCH₃ | H | —CH₂CH₂C₆H₅ |
| 47 | 3-OCH₃ | H | —CH₂CH₂CN |
| 48 | 3,5-di-Cl | H | —C₆H₁₁ |
| 49 | 3,4-di-Cl | H | —CH₂CH₂OC₆H₅ |
| 50 | 4,5-di-Cl | H | —CH₂CH₂C₆H₁₁ |
| 51 | 5-CH₂CH₂C₆H₅ | H | —CH₂C₆H₁₁ |
| 52 | 4-C(CH₃)₃ | H | —CH₂C₆H₅ |
| 53 | 5-Br | H | —(CH₂)₃CH₃ |
| 54 | 5-S(CH₂)₃CH₃ | H | —CH₃ |
| 55 | 3,5-di-C₆H₅ | H | —CH₃ |
| 56 | 3,5-di(C₆H₄—4-CH₃) | H | —CH₃ |
| 57 | 5-(C₆H₄—3-Cl) | H | —CH₃ |
| 58 | 5-(C₆H₄—4-OCH₃) | H | —CH₃ |
| 59 | 4-SC₂H₅ | H | —CH₂CH(OH)CH₂OH |
| 60 | 4-CH₃—5-C₂H₅ | H | —C₆H₅ |
| 61 | H | H | —CH₂C=CHCH=CHO |
| 62 | H | H | —CH₂—(C₆H₁₀—4-CH₂OH) |

TABLE III

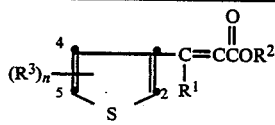

| Example | (R³)ₙ | R¹ | R² |
|---|---|---|---|
| 63 | H | —CH₃ | —C₂H₅ |
| 64 | H | —C₆H₅ | —CH₃ |
| 65 | H | —C₆H₁₁ | —CH₂CH₂CH₃ |
| 66 | 2,5-di-CH₃ | H | —CH₃ |
| 67 | 2,5-di-CH₃ | H | —CH₂CH₂OH |
| 68 | 2,5-di-C₂H₅ | H | —(CH₂)₃OH |
| 69 | 5-C₂H₅ | H | —CH₂CH₂Cl |
| 70 | 4-CH₃ | H | —CH₂CH₂OCH₃ |
| 71 | 5-CH₃ | H | —CH₂C₆H₅ |
| 72 | 2-Cl | H | —CH₂C₆H₁₁ |
| 73 | 2,5-di-C(CH₃)₃ | H | —CH₂CH₂OC₆H₅ |
| 74 | 2,5-di-C₆H₅ | H | —CH₂CH₂CN |
| 75 | 2-Br | H | —CH₂CH₂OCCH₃ (O) |
| 76 | 2,5-di-Br | H | —CH₂CH₂NHCCH₃ (O) |
| 77 | 2-I | H | —C₆H₁₁ |
| 78 | 2-SC₂H₅—5-C₂H₅ | H | —CH₂—C=CHCH=CHO |
| 79 | H | H | —CH₂—CHCH₂CH₂O |

TABLE III-continued

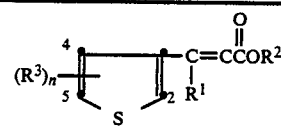

| Example | (R³)ₙ | R¹ | R² |
|---|---|---|---|
| 80 | H | H | —CH₂C₆H₄—4-CH₃ |
| 81 | H | H | —CH₂C₆H₁₀—4-CH₂OH |
| 82 | H | H | —CH₂C₆H₁₀—4-CH₃OCCH₃ (O) |
| 83 | H | H | —C₆H₅ |
| 84 | H | H | —CH₂CH₂CH(CH₃)₂ |
| 85 | H | H | —CH₂CH₂OCOC₂H₅ (O) |
| 86 | H | H | —CH₂CH₂Br |
| 87 | H | H | —CH₂CH₂SCH₂CH₂OH |
| 88 | H | H | —CH₂CH₂OCH₂CH₂OH |

The inherent viscosities (I.V. of the copolyesters described herein are determined according to ASTM D2857-70 procedure in a Wagner Viscometer of Lab Glass Inc. of Vineland, N.J. having a ½ ml capillary bulb, using a polymer concentration of 0.5%, by weight, in 60/40, by weight, phenol/tetrachloroethane solvent. The procedure comprises heating the polymer/solvent system at 120° C. for 15 minutes to enhance dissolution of the polymer, cooling the solution to 25° C. and measuring the time of flow at 25° C. The I.V. is calculated from the equation $$\{\eta\}_{0.50\%}^{25°\,C.} = \frac{\ln \frac{t_s}{t_o}}{C}$$

where:
  $\{\eta\}$ = Inherent viscosity at 25° C. at a polymer concentration of 0.5 g/100 ml of solvent;
  ln = Natural logarithm;
  $t_s$ = Sample flow time;
  $t_o$ = Solvent-blank flow time; and
  C = Concentration of polymer in grams per 100 ml of solvent = 0.50.

The nonextractabilities of the methine residues described herein are determined as follows:

All extractions are done in glass containers with distilled solvents under the time and temperature conditions described below. The sample form is ½ inch × 2½ inch segments cut from the cylindrical side wall portion of 2-liter bottles. All samples are washed with cold solvent to remove surface contaminants and are exposed using 200 ml solvent/100 in.² surface area (2 ml/in.²).

Solvent blanks are run under the same extraction conditions without polymer. In most cases samples were extracted, spiked, with a known amount of additive as a control, and analyzed in duplicates. The solvents employed and the extraction conditions for each solvent are:

1. Water. The samples at room temperature are added to solvent and heated at 250° F. for two hours. Half of the samples are then analyzed and the remainder are placed in a 120° F. oven for 30 days.

2. 50% Ethanol/Water. The samples at room temperature are added to the solvent at room temperature, placed in an oven at 120° F. and analyzed after 24 hours and 30 days.

3. Heptane. The samples at room temperature are added to solvent at room temperature and heated at 150° F. for two hours. Part of the samples are cooled to room temperature and analyzed spectrophotometrically and the remainder are allowed to age at 120° F. for 30 days before analysis.

Any suitable analytical technique and apparatus may be employed to determine the amount of methine residue extracted from the polymer.

The invention has been described in detail with particular reference to preferred embodiments thereof, but it will be understood that variations and modifications can be effected within the spirit and scope of the invention.

We claim:

1. A composition comprising molding or fiber grade condensation polymer having copolymerized therein a total of from 1.0 to abut 10,000 ppm, of the residue of one or a mixture of methine compounds of the formula $$A-\underset{R^1}{\underset{|}{C}}=\underset{CN}{\underset{|}{C}}COR^2$$

wherein A is an unsubstituted or substituted 2-furanyl, 2-thienyl or 3-thienyl radical;

$R^1$ is hydrogen or an unsubstituted or substituted alkyl, cycloalkyl or aryl radical; and $R^2$ is hydrogen or an unsubstituted or substituted alkyl, alkenyl, cycloalkyl or aryl radical.

2. The composition of claim 1 wherein the polymer is a linear polyester and A is a 2-furanyl radical having the structure wherein $R^3$ is alkyl, hydroxyalkyl, alkoxyalkyl, alkanoyloxyalkyl, arylalkyl, cycloalkylalkyl, aryloxyalkyl, cycloalkoxyalkyl, alkylthioalkyl, arylthioalkyl, alkenyl, alkoxy, cycloalkyl, aryl or halogen; and n is 0, 1 or 2.

3. The composition of claim 1 wherein the polymer is a linear polyester having copolymerized therein about 200 to about 800 ppm of the residue of one or a mixture of methine compounds of the formula wherein $R^2$ is lower alkyl.

4. The composition of claim 1 wherein the polymer is a linear polyester and A is a 2-thienyl radical having the structure wherein $R^3$ is alkyl, hydroxyalkyl, alkoxyalkyl, alkanoyloxyalkyl, arylalkyl, cycloalkylalkyl, aryloxyalkyl, cycloalkoxyalkyl, alkylthioalkyl, arylthioalkyl, alkenyl, alkoxy, cycloalkyl, aryl or halogen; and n is 0, 1 or 2.

5. The composition of claim 1 wherein the polymer is a linear polyester having copolymerized therein about 200 to abut 800 ppm of the residue of one or a mixture of methine compounds of the formula wherein $R^2$ is lower alkyl.

6. The composition of claim 1 wherein the polymer is a linear polyester and A is a 3-thienyl radical having the structure wherein $R^3$ is alkyl, hydroxyalkyl, alkoxyalkyl, alkanoyloxyalkyl, arylalkyl, cycloalkylalkyl, aryloxyalkyl, cycloalkoxyalkyl, alkylthioalkyl, arylthioalkyl, alkenyl, alkoxy, cycloalkyl, aryl or halogen; and n is 0, 1 or 2.

7. The composition of claim 1 wherein the polymer is a linear polyester having copolymerized therein about 200 to about 800 ppm of the residue of one or a mixture of methine compounds of the formula wherein $R^2$ is lower alkyl.

8. The composition of any of claims 1-7 wherein the polyester acid moiety is comprised of at least about 50 mol % terephthalic acid residue, and the glycol moiety at least about 50 mol % ethylene glycol or 1,4-cyclohexanedimethanol residue, and the polyester contains a total of from about 2 to about 1,500 ppm of one or a mixture of the methine residues.

9. The composition of any of claims 1-8 wherein the polyester is comprised of from about 75 to 100 mol % terephthalic acid residue and from abut 75 to 100 mol % ethylene glycol residue.

10. The composition of claim 1 wherein the polymer is unsaturated polyester having an acid moiety comprised of fumaric or maleic acid or mixtures thereof and up to abut 60 mol % of one or amixture of o-phthalic, iso-phthalic, or terephthalic acids, and having a glycol moiety comprised of one or a mixture of propylene glycol, neopentyl glycol, 2,2,4-trimethyl-1,3-pentanediol, ethylene glycol or diethylene glycol.

11. The composition of claim 10 wherein the acid moiety is comprised of from about 75 to 100 mol % o-phthalic acid and maleic acid in a mole ratio of from abut ½ to about 2/1, and the glycol moiety is comprised of from about 75 to 100 mol % propylene glycol.

12. The composition of claim 10 containing a curing amount of an ethylenically unsaturated monomer.

13. A cured, formed article of the composition of claim 12.

14. A fiber of the composition of claim 1 dyed with from about 0.01 to about 5.0% by weight based on weight of fiber of a disperse dye.

15. A fiber of the composition of claim 8 dyed with from abut 0.01 to about 5.0% by weight based on weight of fiber of a disperse dye.

16. A formed article of the composition of claim 1.
17. A formed article of the composition of claim 8.
18. A formed article of the composition of claim 9.
19. A formed article of the composition of claim 10.

* * * * *